United States Patent
Jessheim et al.

(10) Patent No.: US 9,856,732 B2
(45) Date of Patent: Jan. 2, 2018

(54) TRACERS

(71) Applicant: RESTRACK AS, Kjeller (NO)

(72) Inventors: Beata Krognes Jessheim, Jessheim (NO); Sissel Opsahl Viig, Oslo (NO); Øyvind Dugstad, Hagan (NO); Helge Stray, Hagan (NO)

(73) Assignee: RESTRACK AS, Kjeller (NO)

( * ) Notice: Subject to any disclaimer, the term of this patent is extended or adjusted under 35 U.S.C. 154(b) by 0 days.

(21) Appl. No.: 14/654,404

(22) PCT Filed: Dec. 23, 2013

(86) PCT No.: PCT/EP2013/077957
§ 371 (c)(1),
(2) Date: Jun. 19, 2015

(87) PCT Pub. No.: WO2014/096459
PCT Pub. Date: Jun. 26, 2014

(65) Prior Publication Data
US 2016/0003040 A1    Jan. 7, 2016

(30) Foreign Application Priority Data
Dec. 21, 2012 (NO) .................................. 20121558

(51) Int. Cl.
*E21B 49/08* (2006.01)
*G01N 33/28* (2006.01)
(Continued)

(52) U.S. Cl.
CPC ............... *E21B 49/08* (2013.01); *B09C 1/00* (2013.01); *C09K 8/58* (2013.01); *E21B 47/1015* (2013.01);
(Continued)

(58) Field of Classification Search
None
See application file for complete search history.

(56) References Cited

U.S. PATENT DOCUMENTS 3,008,521 A * 11/1961 Boucher ................. E21B 49/10
166/101
3,590,923 A *  7/1971 Cooke, Jr. ............... E21B 49/00
166/252.6
(Continued)

FOREIGN PATENT DOCUMENTS

WO       2011063023 A2    5/2011

OTHER PUBLICATIONS

Feb. 25, 2014—(WO) International Search Report and Written Opinion—APP PCT/EP2013/077957.
(Continued)

*Primary Examiner* — Jeffrey Washville
(74) *Attorney, Agent, or Firm* — Banner & Witcoff, Ltd.

(57) ABSTRACT

A family of organic tracers is proposed for inter-well measurement of residual oil in petroleum reservoirs, as is their use as partitioning tracers in a petroleum reservoir. The tracers consist of at least one benzyl alcohol of formula i)
(Continued)

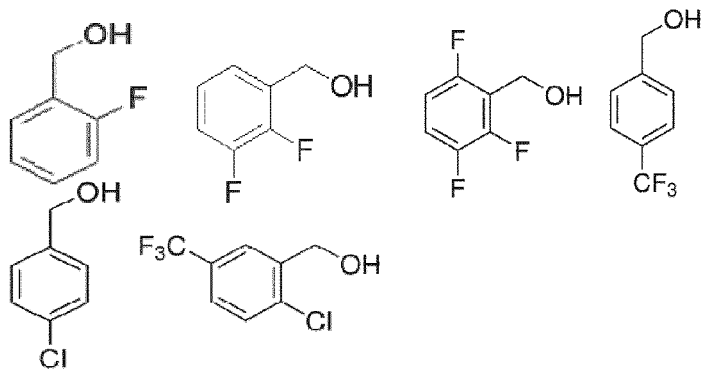

Examples of chemical structures of compounds from the six groups: monofluoro, difluoro, trifluoro, trifluoromethyl benzyl alcohol and monochloro and monochlor-(trifluoromethyl) benzyl alcohol.

wherein each of $R_1$ to $R_5$ is independently selected from H, F, Cl, Br, I, $CF_3$, $CF_2Cl$, $CFCl_2$ and $CCl_3$ and wherein at least one of $R_1$ to $R_5$ is not H.

i)

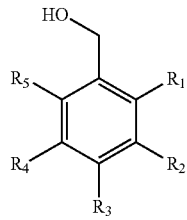

5 Claims, 5 Drawing Sheets

(51) Int. Cl.
    *C09K 8/58*     (2006.01)
    *B09C 1/00*     (2006.01)
    *E21B 47/10*     (2012.01)

(52) U.S. Cl.
    CPC .......... *G01N 33/28* (2013.01); *G01N 33/2823* (2013.01)

(56) References Cited

U.S. PATENT DOCUMENTS

| | | |
|---|---|---|
| 5,168,927 A | 12/1992 | Stegemeier et al. |
| 5,256,572 A * | 10/1993 | Tang ............... E21B 47/1015 166/252.2 |
| 5,905,036 A | 5/1999 | Pope et al. |
| 7,704,746 B1 | 4/2010 | White et al. |
| 2003/0006036 A1 * | 1/2003 | Malone ............... E21B 47/1015 166/250.12 |
| 2007/0215385 A1 | 9/2007 | Anderson |
| 2010/0307745 A1 | 12/2010 | Lafitte et al. |

OTHER PUBLICATIONS

Jin, M., et al, Partitioning tracer test for detection, estimation and remediation performance assessment of subsurface nonaqueous phase liquids, . Water resources research, 1995. 31(5): p. 1201-1211.
Deans, H.H., Using chemical tracers to measure fractional flow and saturation in-situ, in Fitlh Symposium on Improved Methods for Oil Recovery of the Society of Petroleum Engineers of AIME held in Tulsa, Oklahoma, Apr. 16-19, 1978. 1978, SPE: Tulsa, Oklahoma.
Lichtenberger, G.J., Field Applications of Interwell Tracers for Reservoir Characterization of Enhanced Oil Recovery Pilot Areas, in SPE Production Operations Symposium1991, Society of Petroleum Engineers: Oklahoma City, Oklahoma.
Zemel, B., Tracers in Oil Field 1994, New York: Elsevier.
Dias, F.F., Alexander, M, Effect of Chemical Structure on the Biodegradability of Aliphatic Acids and Alcohols. . Applied Microbiology 22: p. 1114-1118.
Yang, H., et al., Aromatic Compounds Biodegradation under Anaerobic Conditions and their QSBR Models. . Science of the Total Environment 358: p. 265-276.
Setarge, B., et al, Partitioning and Interfacial Tracers to Characterize Non-Aqueous Phase Liquids (NAPLs) in Natural Aquifer Material. . Phys. Chem. Earth (B) 1999. 24: p. 501-510.

* cited by examiner

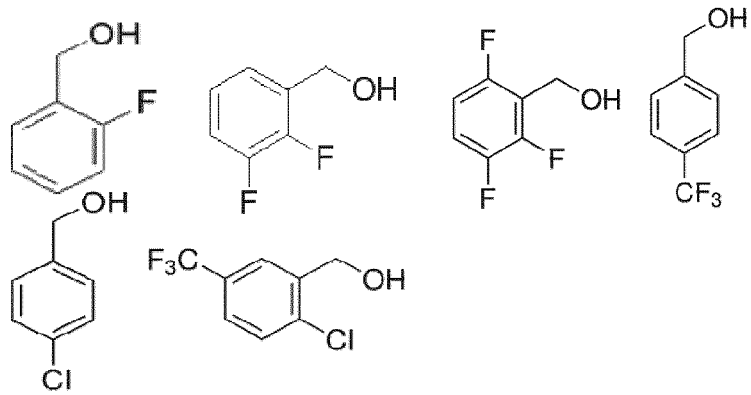
Figure 1. Examples of chemical structures of compounds from the six groups: monofluoro, difluoro, trifluoro, trifluoromethyl benzyl alcohol and monochloro and monochlor-(trifluoromethyl) benzyl alcohol.
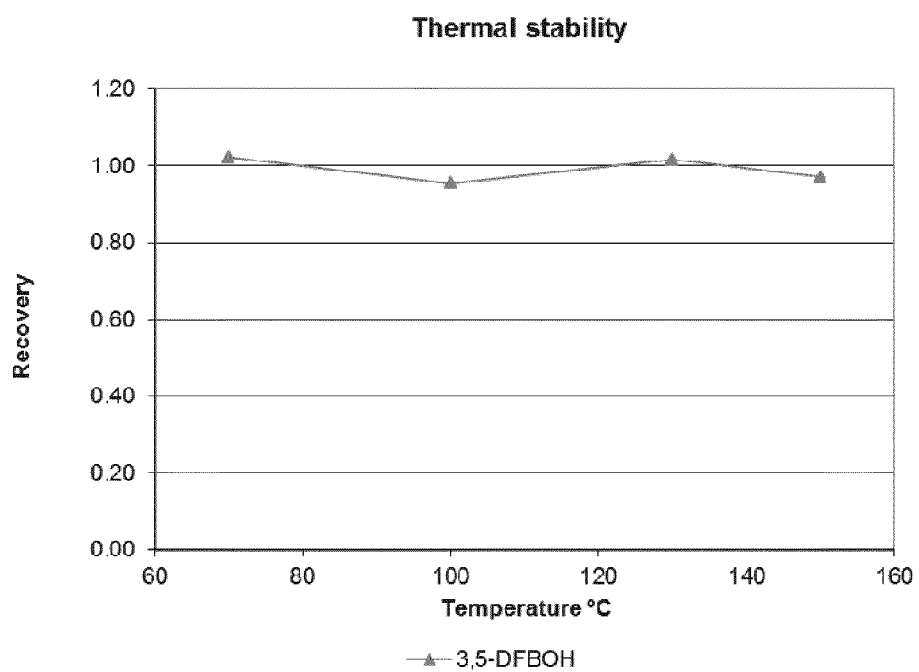
Figure 2. Results for thermal stability tests carried out for eight weeks.

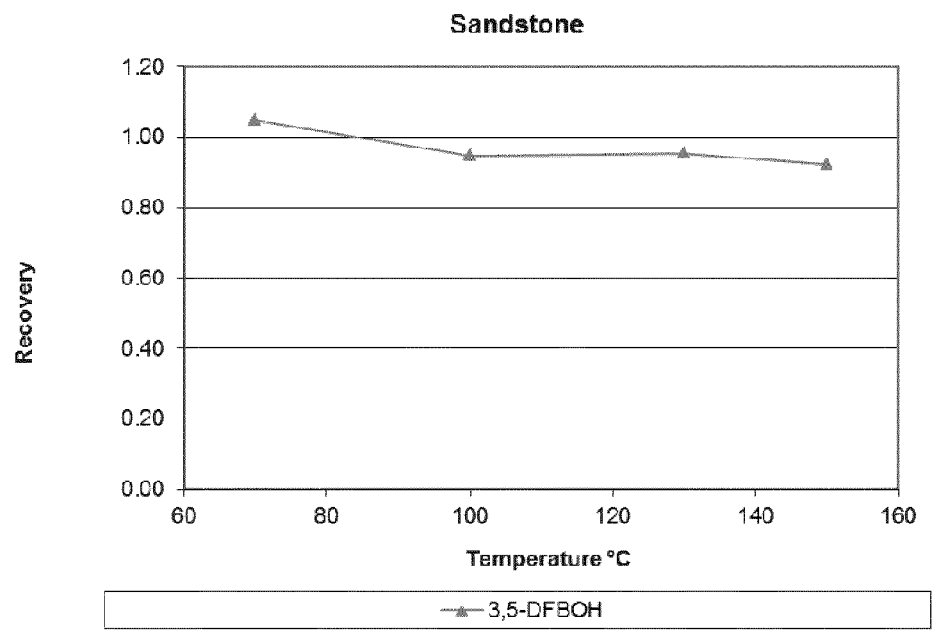
Figure 3. Results for sorption tests with sandstone carried out for eight weeks.
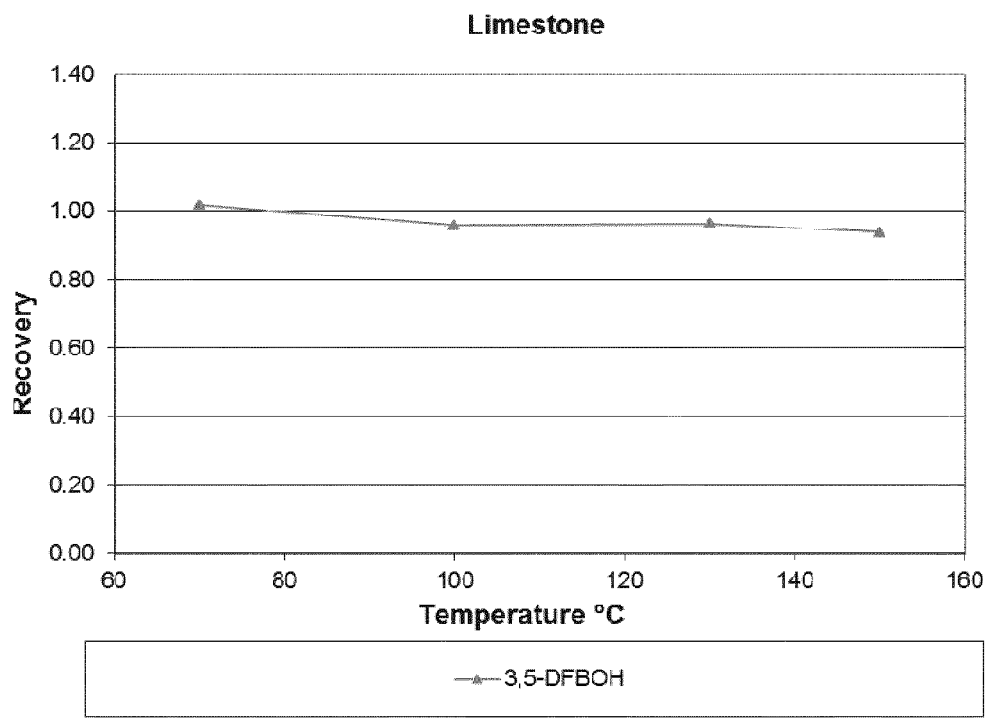
Figure 4. Results for sorption tests with limestone carried out for eight weeks.

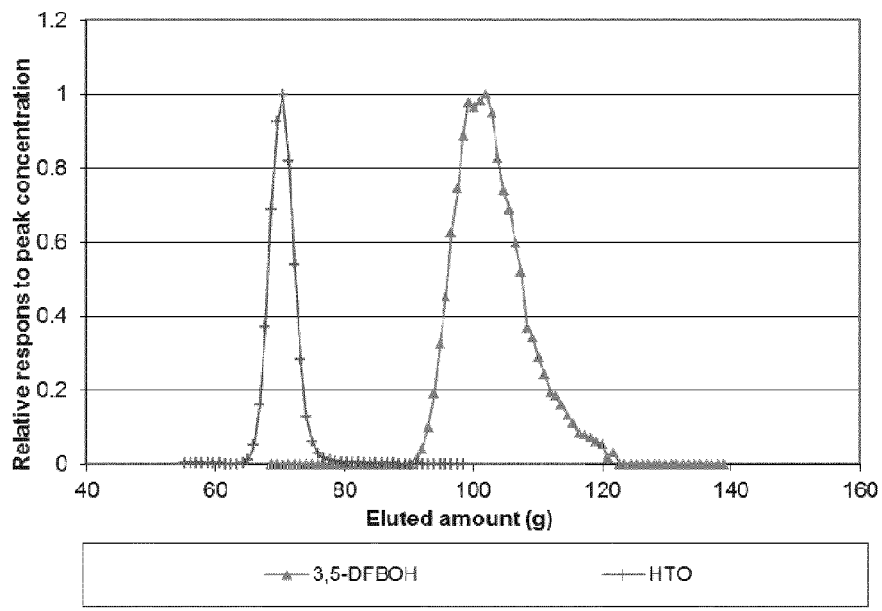
Figure 5. Results from dynamic experiments on a residual oil saturated column with oil 1 and water composition 1 at 80°C.
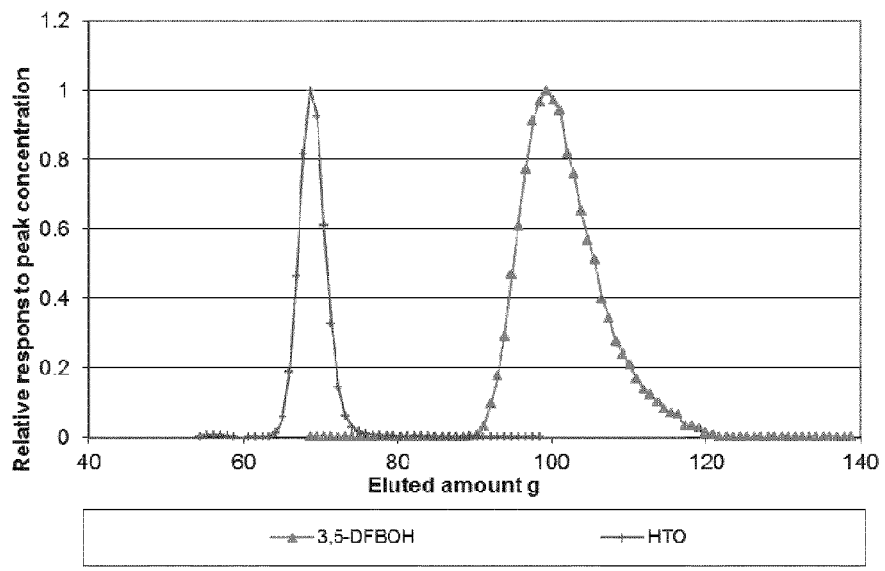
Figure 6. Results from dynamic experiments on a residual oil saturated column with oil 1 and water composition 1 at 107°C.

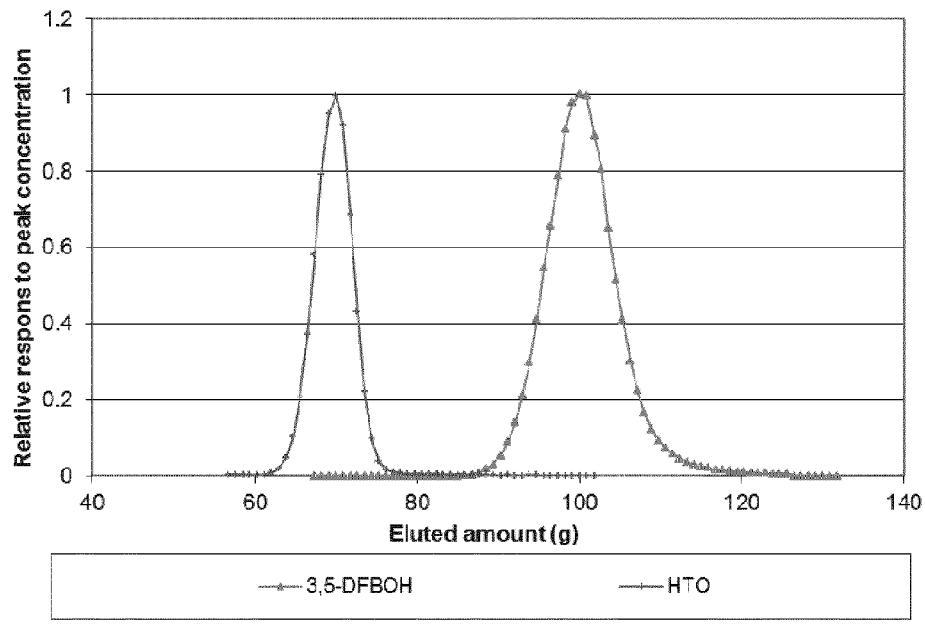
Figure 7 Results from dynamic experiments on a residual oil saturated column with oil 2 and water composition 2 at 40°C.
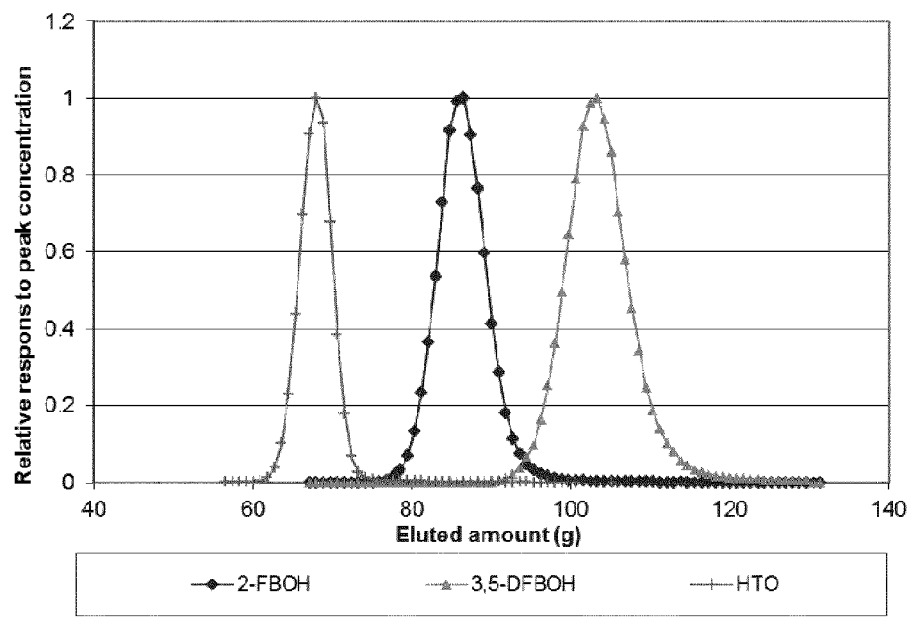
Figure 8. Results from dynamic experiments on a residual oil saturated column with oil 2 and water composition 2 at 80°C.

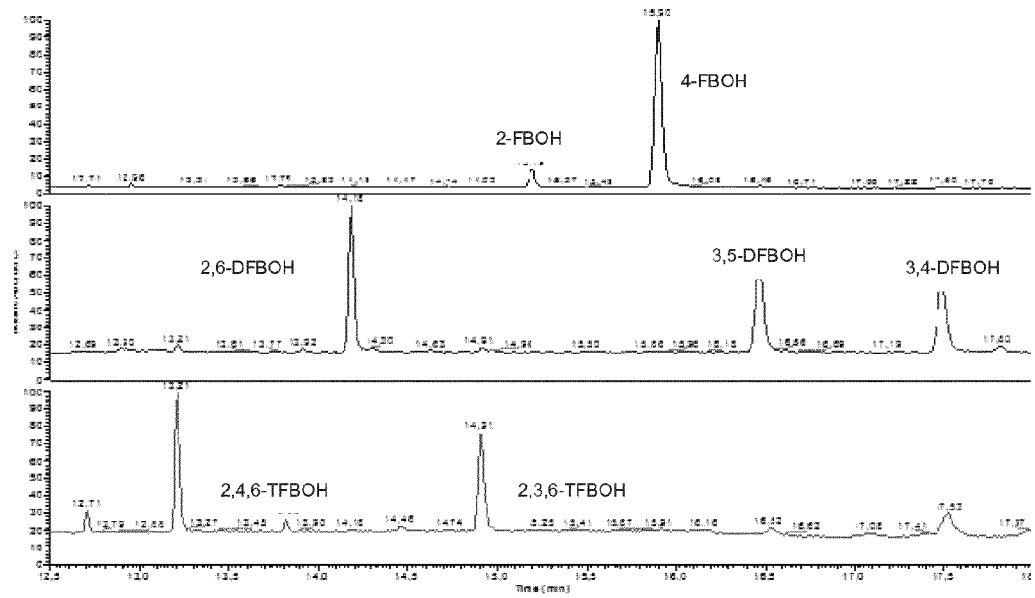
Figure 9. Chromatograms of a 500 ppt standard solution of selected fluorinated benzyl alcohols. 4-FBOH is used as internal standard and have a higher concentration.
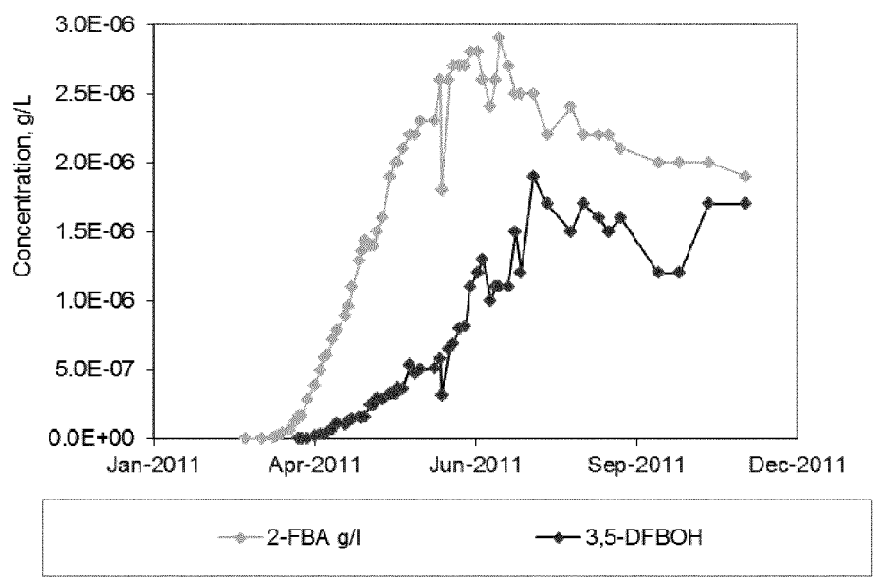
Figure 10. Results from a field test with a selected tracer candidate 3,5-DFBOH (bottom line) in comparison with 2-FBA (top line).

TRACERS

The present application is a U.S. Natioal Phase of International Application No. PCT/EP2013/077957, filed on Dec. 23, 2013, designating United States of America, and claims priority to Norwegian Patent Application No. 20121558, filed Dec. 21, 2012. This application claims priority to and the benefit of the above-identified applications, each of which is fully incorporated by reference herein.

FIELD OF THE INVENTION

The present invention relates to tracers useful for measurement of residual oil in petroleum reservoirs. In particular, the present invention relates to partitioning tracers suitable for such measurements.

BACKGROUND OF THE INVENTION

Institute for Energy Technology in Norway (IFE) has, since the nineteen sixties, worked with development of tracer technology for industrial applications. Since the beginning of the nineteen eighties the focus has been on the oil and gas industry. Many passive inter-well (well-to-well) tracers have been tested and qualified, and in recent years, some families of partitioning tracers have also been tested in laboratory and field experiments. The laboratory tests include flooding experiments at simulated reservoir conditions using sand-packed columns containing crude oil at residual oil saturation. The tracer candidates are also tested for thermal stability, and adsorption in closed vials with anaerobe atmosphere, with and without rock materials present.

Partitioning tracers are simultaneously injected with a passive tracer as a pulse in partitioning inter-well tracer tests (PITT). Due to the solubility of the partitioning tracers in the oil phase, these tracers will move more slowly through the reservoir than the non-retained passive tracer. When the oil/water partition coefficient for the partitioning tracer is known, the residual oil saturation can be calculated when the difference in migration times for the passive and the partitioning tracers have been measured.

The Partitioning Inter-well Tracer Test (PITT) technology has potential to become a standard method for identifying enhanced oil recovery (EOR) targets, and for evaluation of performance of EOR operations. PITTs have successfully been applied in some oil fields producing at marginal oil rates. The Partitioning Inter-well Tracers Tests to determine residual oil saturation is based on chromatographic separation of tracers in the reservoir [1],[2],[3]. Tracers with different oil/water partition coefficients are introduced with injection water, and samples of water are collected from the production stream for analysis. The tracers will move through the reservoir at different velocities depending on the partition coefficients and the oil saturation in the volume between injection and production wells. The oil saturation for a field with negligible oil flow rates compared to the water flow rates (a field close to residual oil saturation) can be described by chromatographic theory and calculated from the following equation:

$$S = \frac{T_R - T_R^W}{T_R + T_R^W(K-1)} \quad \text{(equation 1)}$$

Here $T_R$ and $T_R^W$ are the retention times of the partitioning and passive water tracer, respectively, S is the residual oil saturation, and K is the partition coefficient of the partitioning tracer.

If the partition coefficient is known, the residual oil saturation can be calculated from the measured difference in the arrival times between a non-partitioning (passive) and a partitioning tracer. This equation is only valid as long as the tracers do not interact with the rock material. Different groups of chemicals have been tested for application as partitioning tracers. Important parameters are the partition coefficient, the thermal stability, the absence of adsorption to rock materials and the analytical detectability.

Certain compounds, such as alcohols, have been used as partitioning tracers to estimate amounts of non-aqueous phase liquid in porous media and remaining oil in the swept area between wells (e.g. McClesky sandstone field test, Landmark method, Leduc test, Ranger field test, [5]). However, many alcohols are naturally present in oil reservoirs, making them difficult to detect at low level and/or distinguish from naturally occurring compounds. Furthermore, while radiolabeled compounds could be used and detected with high sensitivity, such compounds should be avoided due to regulatory restrictions in many areas.

In order to be effective as a partitioning tracer, a compound must display certain key properties for effective function. In particular, an effective partitioning tracer should display an appropriate partition coefficient, should be stable to the temperature conditions of the reservoir, should be environmentally acceptable, should not interact with rock and other material of the oil well and oil field, or should do so in an insignificant or predictable way, and/or should be detectable at low level. Suitable compounds would also advantageously be distinct from the compounds found naturally in oil reserves, such that injected compound can be identified as such down to a low level.

It would be of considerable value to provide new oil field tracer compounds which were not naturally present in that environment and which show partitioning between oil and aqueous phases. Such compounds would advantageously be environmentally acceptable, stable to oil reservoir conditions, show little, or preferably no interaction with oil field materials, have predictable partition to the oil phase and/or be detectable at low levels.

SUMMARY OF INVENTION

The present inventors have now established that certain halogenated benzyl alcohol compounds show good oil/water partitioning properties and are not naturally present in an oil field environment. The compounds further provide some or all of the other desirable features of effective partitioning tracers, as described herein.

In a first aspect, the present invention therefore provides the use of at least one benzyl alcohol of formula i) as a partitioning tracer in a petroleum reservoir.

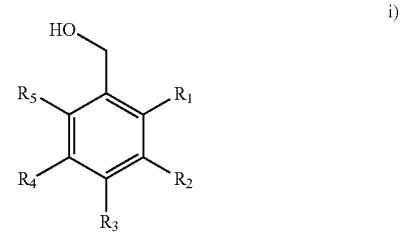

In formula i), each of $R_1$ to $R_5$ is independently selected from H, F, Cl, Br, I, $CF_3$ $CF_2Cl$, $CFCl_2$ and $CCl_3$ and at least one of $R_1$ to $R_5$ is not H. Thus, at least one of groups $R_1$, $R_2$, $R_3$, $R_4$ and/or $R_5$ is a halogenated group such as F, Cl, Br, I, $CF_3$ $CF_2Cl$, $CFCl_2$ or $CCl_3$. More than one of groups of $R_1$ to $R_5$ may be a halogenated group and any two may be the same or different. Preferred groups $R_1$ to $R_5$ include H, Cl, F, Br, $CF_3$ $CF_2Cl$, $CFCl_2$ and $CCl_3$. Particularly preferred groups $R_1$ to $R_5$ include H, F and Cl. It is preferred that at least one of groups $R_1$ to $R_5$ is hydrogen, preferably at least two of groups $R_1$ to $R_5$ are hydrogen.

The tracers of the present invention may advantageously be used, in combination with each other and/or in combination with other tracers, to assess the residual oil saturation of an oil field as described herein. In a further aspect, the invention therefore further provides a method of assessing the oil saturation of an oil field having an injection well and a production well, said method comprising:
a) injecting at least a first tracer having a first partition coefficient and at least a second tracer having a second oil/water partition coefficient into said injection well;
b) measuring the presence and/or concentration of said first tracer and said second tracer in produced water from said production well;
c) determining the retention times for each of said first tracer and said second tracer;
d) relating the retention times and partition coefficients of each of said first and second tracers to the oil saturation of said oil field whereon said first tracer, and optionally said second tracer is a benzyl alcohol of formula i)

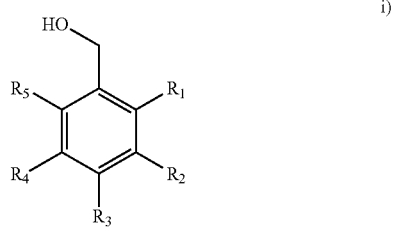

wherein each of $R_1$ to $R_5$ is independently selected from H, F, Cl, Br, I, $CF_3$ $CF_2Cl$, $CFCl_2$ and $CCl_3$ and wherein at least one of $R_1$ to $R_5$ is not H. Suitable benzyl alcohol tracers for use in the method of the invention include all such tracer compounds described herein.

Typically the first tracer will be a "partitioning" tracer, having a first partition coefficient of around 0.5 to 20 (between oil and sea water at 80° C.). Typically the second tracer will be a "passive" tracer. Common passive tracers include fluorinated benzoic acids (e.g. 2-fluorobenzoic acid, 4-fluorobenzoic acid, 2,6-difluorobenzoic acid, 2,4,5-trifluorobenzoic acid and others). These are well studied and their properties are well known to those of skill in the art. In one embodiment the "passive" tracer may have a second partition coefficient of less than $10^{-2}$, e.g. less than $10^{-3}$, such as less than $10^{-4}$, less than $10^{-5}$ or less than $10^{-6}$ (between seawater and oil at 80° C.).

In an alternative embodiment, the second tracer may be a "partitioning" tracer and may be a tracer of the present invention. The first and second tracers will have different partition coefficients. Preferably the first tracer will have a partition coefficient of no less than 1 and the second tracer will have a partition coefficient of no more than 0.5 (between oil and seawater at 80° C.).

In on advantageous aspect, the invention may additionally comprise injecting at least one additional tracer. In this aspect a third tracer having a third partition coefficient may be administered in step a) and included in the measurement, determination and calculation steps b) to d). Generally, each tracer will have a different partition coefficient. Typically only one tracer will be a "passive" tracer. Any third or further tracers may be tracers of formula i) as described herein.

Although described herein as "first" and "second" tracers, as well as subsequent tracers, the order of injection of the tracers need not be according to this nomenclature. For example, in one embodiment, all tracers may be injected simultaneously. Alternatively, the first and second tracers may be injected sequentially in either order. Where more than two tracers are used, any two or more may be injected simultaneously. In one embodiment, the first tracer injected is the tracer with lowest partition coefficient (e.g. a "passive" tracer).

The present invention is directed to the use of halogenated benzyl alcohols as partitioning tracers for use in inter-well tracer tests or in other operations for non-aqueous phase liquid quantification measurements. The fluorinated benzyl alcohols are particularly useful as partitioning tracers in inter-well tracer tests because of high thermal and biological stability and low adsorption to rock material. The compounds are unique in the environment of oil and gas reservoirs, and they can be detected at extremely low concentrations using sophisticated analytical techniques. The partition coefficients of the tracers are ideal for inter-well tracer tests. The tracers come in the same environmental category as fluorinated benzoic acids that are frequently used as passive water tracers today and are considered environmentally acceptable.

BRIEF DESCRIPTION OF THE DRAWINGS AND TABLES

FIG. 1 shows examples of chemical structures of compounds from the groups: monofluoro, difluoro, trifluoro, trifluoromethyl, monochloro and monochloro-(trifluoromethyl) benzyl alcohol. These constitute preferred but not limiting examples of compounds suitable for the various aspects of the invention.

FIG. 2 shows the results for a selected example tracer candidate from thermal stability tests carried out for eight weeks.

FIG. 3 shows the results for a selected tracer candidate from sorption tests with sandstone carried out for eight weeks.

FIG. 4 shows the results for a selected tracer candidate from sorption tests with limestone carried out for eight weeks.

FIG. 5 shows the results for a selected tracer candidate from dynamic experiments on a residual oil saturated column. The column was packed with silica and had a length of 2 m and an internal diameter of 11.1 mm. The test was performed with oil 1 and water 1 at 80° C.

FIG. 6 shows the results for a selected tracer candidate from dynamic experiments on a residual oil saturated column. The column was packed with silica and had a length of 2 m and an internal diameter of 11.1 mm. The test was performed with oil 1 and water 1 at 107° C.

FIG. 7 shows the results for a selected tracer candidate from dynamic experiments on a residual oil saturated column. The column was packed with silica and had a length of 2 m and an internal diameter of 11.1 mm. The test was performed with oil 2 and water 2 at 40° C.

FIG. 8 shows the results for two selected tracer candidates from dynamic experiments on a residual oil saturated column. The column was packed with silica and had a length of 2 m and an internal diameter of 11.1 mm. The test was performed with oil 2 and water 2 at 80° C.

FIG. 9 shows the chromatograms of a 500 ppt standard solution of selected fluorinated benzyl alcohols. 4-FBOH is used as internal standard and has a higher concentration.

FIG. 10 shows the results from a field test with a selected fluorinated benzyl alcohol (top trace) as partitioning tracer injected together with the passive water tracer 2-FBA (bottom trace).

TABLE 1 shows the calculated partition coefficients from a flooding experiment on a silica-packed column with residual oil saturation for two fluorinated benzyl alcohols. Measurements at 80° C.

TABLE 2 shows the results from screening of environmental properties for five selected fluorinated benzyl alcohols.

DETAILED DESCRIPTION

Halogenated alcohols are both unique in the reservoir environment and more chemically and biologically stable than corresponding molecules without halogen atoms. There are several references in the literature to the biodegradability of alcohols [6], [7], [8]. Previous experience with per-deuterated butanol as partitioning tracer at IFE and information found in the literature indicate that presence of halogen atoms in the molecules will lead to less biodegradation of the selected alcohols.

Structural formulas of examples of compounds from four groups of fluorinated benzyl alcohols tested are shown herein, including in FIG. 1. The compounds could be analyzed using gas chromatography with mass spectrometric detection (GC-MS) in produced water after clean-up and pre-concentration of the water samples. Detection limits of 50 ng/l (ppt) could be obtained depending on the level of interferences from the sample matrix. Several compounds from the four groups were selected and tested for thermal stability, flooding properties, and adsorption to rock materials. In addition, two pilot field tests were initiated. Some results from the laboratory tests are shown in Table 1 and in FIG. 2 to FIG. 10. Partition coefficients were measured at 80° C., oil 2 and water 2.

TABLE 1

Examples of measured partition coefficients, K-values, at given conditions

| Name | K |
|---|---|
| 2-FBOH | 1.5 |
| 2,6-DFBOH | 1.5 |
| 3,5-DFBOH | 2.9 |
| 3,4-DFBOH | 2.1 |
| 2,4,6-TFBOH | 2.4 |
| 2,3,6-TFBOH | 1.9 |

A selection of compounds have been submitted for standard environmental tests and have come in the same classification as the fluorinated benzoic acids which are currently permitted for use as passive water tracers, thus allowing their use in field experiments. Since the partition coefficients for these compounds are relatively low, there is little risk of bioaccumulation.

Isomers from the mono-, di- and trifluorobenzyl alcohols as well as the fluoromethyl benzyl alcohols have been tested successfully as representative partitioning tracers. Chlorinated benzyl alcohols and combinations of chlorinated and fluorinated benzyl alcohols are predicted to function well due to similar chemical properties.

The present invention relates to the use of at least one benzyl alcohol of formula i) as a partitioning tracer in a petroleum reservoir, as well as to the corresponding compounds for that use. Compounds of formula i) have the general formula:

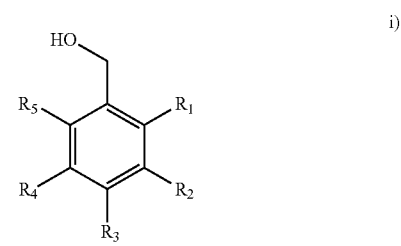

wherein each of $R_1$ to $R_5$ is independently selected from H, F, Cl, Br, I, $CF_3$, $CF_2Cl$, $CFCl_2$ and $CCl_3$ and wherein at least one of $R_1$ to $R_5$ is not H. Preferred R groups include those indicated herein.

Particular examples of compounds of formula i) which are suitable for use in all aspects of the present invention include at least one fluorinated benzyl alcohol of formulae F1 to F24 or of formula F25 or F26. Similarly at least one of F1 to F26 may be used:

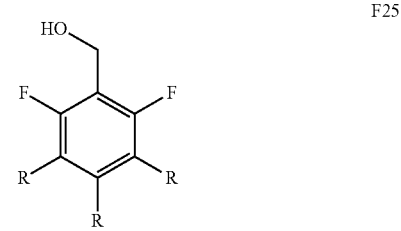

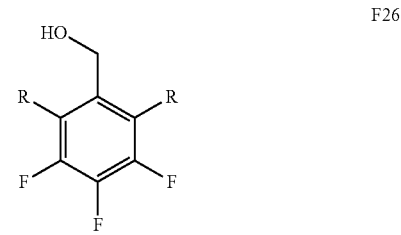

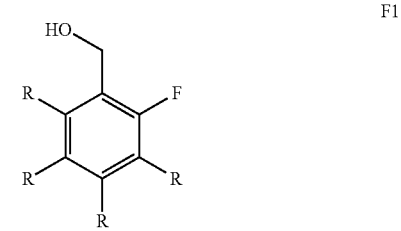

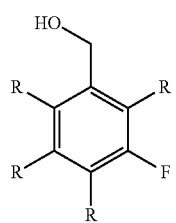 F2
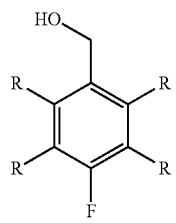 F3
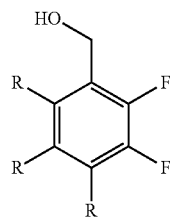 F4
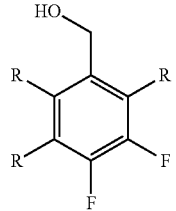 F5
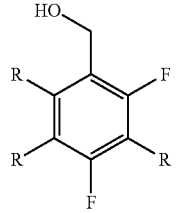 F6
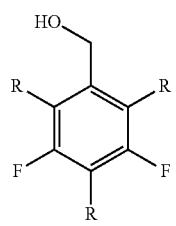 F7
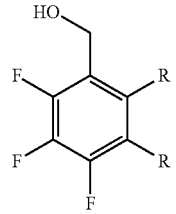 F8
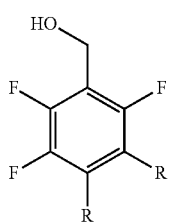 F9
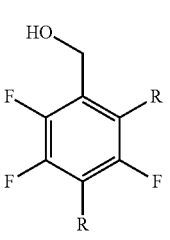 F10
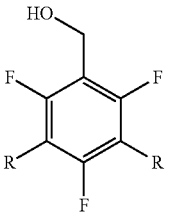 F11
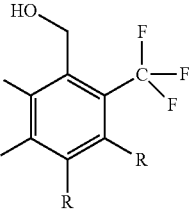 F12
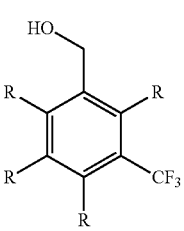 F13
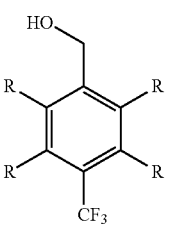 F14
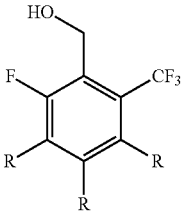 F15

F16 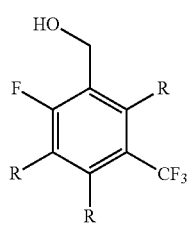

F17 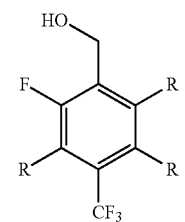

F18 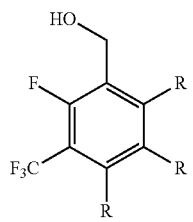

F19 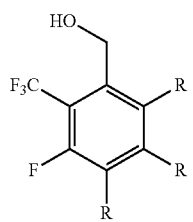

F20 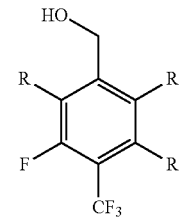

F21 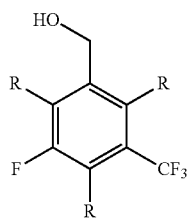

F22 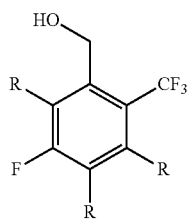

F23 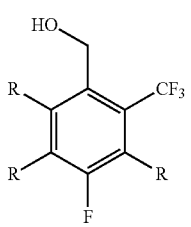

F24 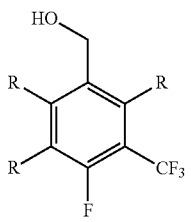

wherein each R group is independently selected from H, Cl, Br, I, $CF_2Cl$, $CFCl_2$ and $CCl_3$. Preferably each R group is independently selected from H and Cl. In one embodiment, all R groups in formulae F1 to F24, as well as optionally in F25 and F26, are hydrogen. In one embodiment 1, 2 or 3 R groups of formulae F1 to F24, as well as optionally F25 and F26, are Cl. The remaining R groups may be any specified herein but will preferably be H.

Further particular examples of compounds of formula i) which are suitable for use in all aspects of the present invention include at least one chlorinated benzyl alcohol of formulae Cl1 to Cl24 or of formula Cl25 or Cl26 Similarly at least one of F1 to F26 may be used:

Cl1 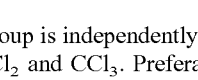

Cl2

Cl3

| | |
|---|---|
| 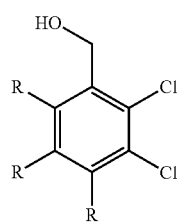 Cl4 | 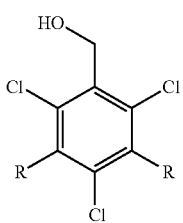 Cl11 |
| 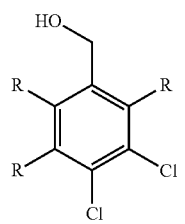 Cl5 | 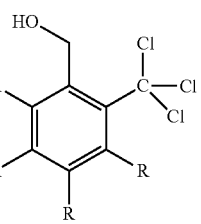 Cl12 |
| 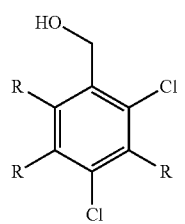 Cl6 | 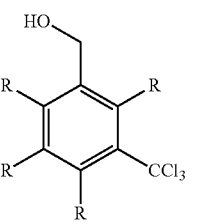 Cl13 |
| 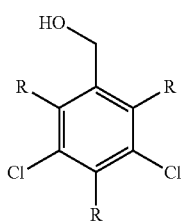 Cl7 | 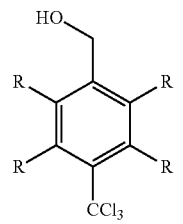 Cl14 |
| 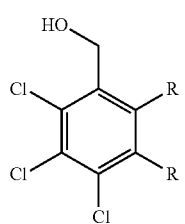 Cl8 | 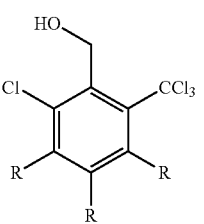 Cl15 |
| 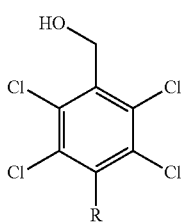 Cl9 | 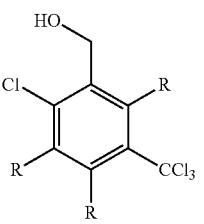 Cl16 |
| 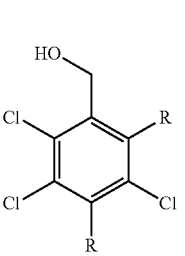 Cl10 | 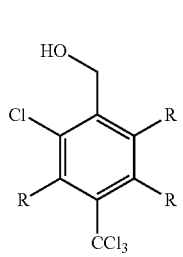 Cl17 |

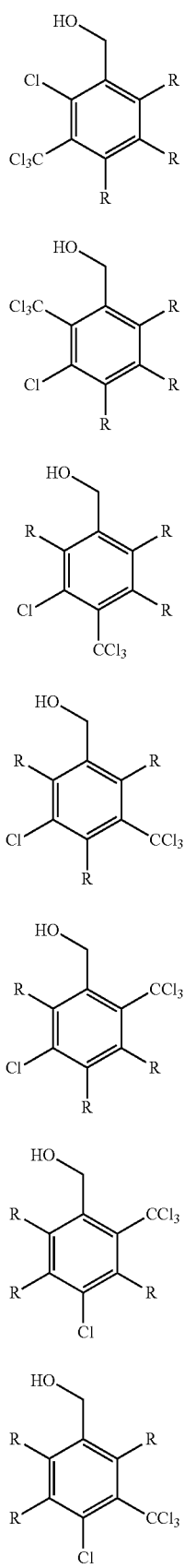

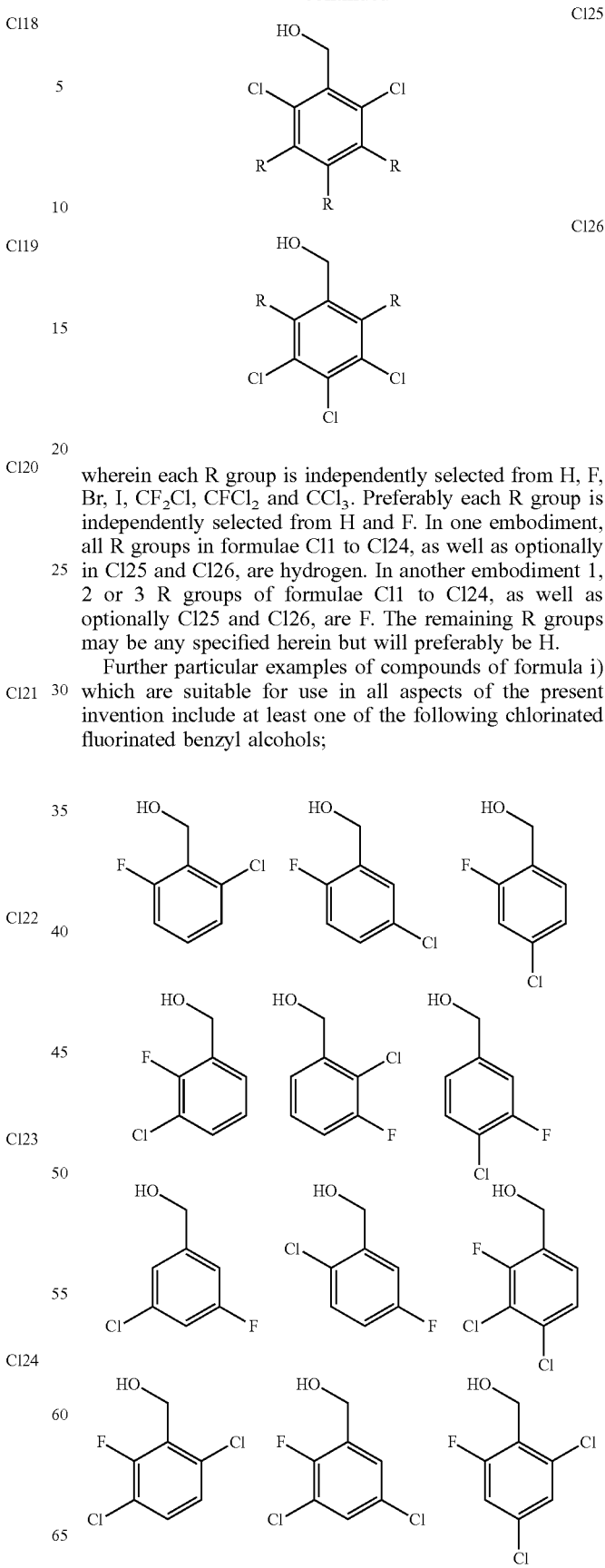

wherein each R group is independently selected from H, F, Br, I, $CF_2Cl$, $CFCl_2$ and $CCl_3$. Preferably each R group is independently selected from H and F. In one embodiment, all R groups in formulae Cl1 to Cl24, as well as optionally in Cl25 and Cl26, are hydrogen. In another embodiment 1, 2 or 3 R groups of formulae Cl1 to Cl24, as well as optionally Cl25 and Cl26, are F. The remaining R groups may be any specified herein but will preferably be H.

Further particular examples of compounds of formula i) which are suitable for use in all aspects of the present invention include at least one of the following chlorinated fluorinated benzyl alcohols;

-continued

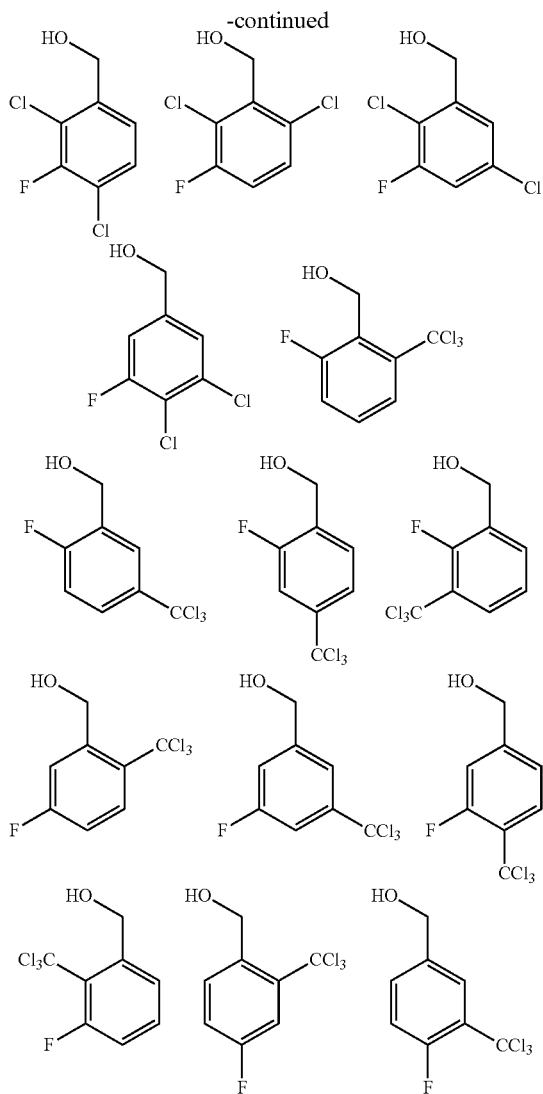

The Cl and F groups in the above formulae may evidently be exchanged such that F may be present in place of Cl and vice versa.

In one preferred embodiment of the invention, the compounds of formula i) which are suitable for use in all aspects of the present invention are the compounds shown in FIG. 1.

In a further, highly effective embodiment compatible with all aspects of the invention, the benzyl alcohol is at least one selected from 2-fluorobenzyl alcohol (2-FBOH), 2,6-difluorobenzyl alcohol (2,6-DFBOH), 3,5-difluorobenzyl alcohol (3,5-DFBOH), 3,4-difluorobenzyl alcohol (3,4-DFBOH), 2,4,6-trifluorobenzyl alcohol (2,4,6-TFBOH) and 2,3,6-trifluorobenzyl alcohol (2,3,6-TFBOH).

The halogenated benzyl alcohols for use in the various aspects of the present invention are typically highly stable in aqueous solution and such stability is a considerable advantage since degradation reduces the concentration of tracer available for detection.

Preferably, the compounds of formula i) (and the preferred compounds as indicated herein) are stable in water at concentration levels typical in water samples from oil reservoirs (typical concentration level is 50 ppt to 100 ppb) for at least 4 weeks at reservoir temperatures. Preferably such compounds are stable for at least 6 weeks, preferably at least 8 weeks under such conditions. Preferably, this stability will be exhibited at temperatures of at least 80° C., more preferably at least 100° C., most preferably at temperatures of at least 150° C. "Stable" in this context may be taken as having a concentration of tracer compound within 20% of the starting concentration as measured by GC-MS, more preferably within 10%.

A further key feature of the compounds used in the various aspects of the present invention is their high detectability. Specifically, the compounds of formula i) (and the preferred compounds as indicated herein) are preferably detectable by GC-MS down to a concentration of 500 ppt (parts per trillion) or lower. Preferably this detection limit will be 100 ppt or lower, more preferably 50 ppt or lower. It is possible for the detection limit to be still lower, such as 1 ppt or 100 ppb.

A still further important feature of the compounds used in the various aspects of the present invention is their relatively low environmental impact. Specifically, the compounds of formula i) (and the preferred compounds as indicated herein) are preferably classified as "red" or better (e.g. "red" or "yellow") according to the HOCNF (Harmonized Offshore Chemical Notification Format for chemicals released to the North Sea) testing criteria.

A yet further feature of the compounds used in the various aspects of the present invention is their low reaction with and sorption onto materials typically found in oil fields such as rock, particularly limestone and/or sandstone. Specifically, the compounds of formula i) (and the preferred compounds as indicated herein) will typically be stable in the presence of sandstone and/or limestone for at least a month, more preferably at least two months under aqueous conditions at temperatures corresponding to oil reservoir temperatures. Preferably, this stability will be exhibited at temperatures of at least 80° C., more preferably at least 100° C., most preferably at temperatures of at least 150° C. "Stable" in this context may be taken as having a concentration of tracer compound within 20% of the starting concentration as measured by GC-MS, more preferably within 10%.

A still further feature of the benzyl alcohol compounds used in the various aspects of the present invention is their highly suitable partition coefficients. For example, compounds of formula i) or preferred compounds as described herein may have partition coefficients between 1.0 and 8.0. The partition coefficients should not be too high because the partitioning tracers then will be retained too much compared to the passive water tracer. Preferable values for the partition coefficients will be between 1.2 and 7, preferably between 1.3 and 5. The partition coefficients of two example compounds at given conditions are shown in Table 1 herein. In all cases referred to herein partition coefficients are measured at 80° C., oil 2 and water 2, unless otherwise stated.

One important aspect of the present invention relates to a method of assessing the oil saturation of an oil field (petroleum reservoir) having an injection well and a production well, said method comprising:

a) injecting at least a first tracer having a first partition coefficient and a second tracer having a second partition coefficient into said injection well;

b) measuring the presence and/or concentration over time of said first tracer and said second tracer in produced water from said production well;

c) determining the retention times for each of said first tracer and said second tracer d) relating the retention times and partition coefficients of each of said first and second tracers to oil saturation of said oil field.

In such a method, at least the first tracer will be a "partitioning tracer" and will be a halogenated benzyl alcohol such as any of those described herein. This will be a "partitioning" tracer and may have a partition coefficient as described herein. The second tracer may also be a benzyl alcohol, such as those described herein but will typically have a different partition coefficient from the first tracer. Most commonly the second tracer (which may be injected before, after or simultaneously with the first tracer) will have a lower partition coefficient and may be a "passive" tracer.

Another possibility will be to inject a passive tracer (tracer 2) and two or more partitioning tracers (where at least one and optionally both may be of the invention). The partitioning tracers will have different partition coefficients. Partitioning tracers will be selected based among other things on their degree of partitioning. The distance between injector and producer as well as the assumed oil saturation between the well pair will be considered when selecting the partitioning tracers. One of the selected partitioning tracers will be a benzyl alcohol as described herein while the other partitioning tracers may be benzyl alcohols or other suitable partitioning tracers. Such tracers are known in the art.

In one preferred embodiment, the first tracer is a tracer of formula I as described herein and the second tracer is a "non-partitioning", "passive" or "passive water" tracer. It is not essential that one tracer be a "passive" tracer but this forms one preferred embodiment. If one tracer is a "passive" tracer and if the partition coefficients for the partitioning tracers are known, the residual oil saturation can be calculated or estimated from the measured difference in the arrival times between the passive tracer and the partitioning tracer using equation 1 as described herein.

$$S = \frac{T_R - T_R^W}{T_R + T_R^W(K-1)} \quad \text{(equation 1)}$$

Where $T_R$ and $T_R^W$ are the retention times of the partitioning and passive water tracer, respectively (in this case tracer 1 and tracer 2 if the latter is a passive tracer), S is the residual oil saturation, and K is the partition coefficient of the partitioning tracer (e.g. see Table 1).

More general equations may be formulated for situations where all tracers are partitioning tracers and other equations and approximations which can be used in calculating residual oil saturation are well known. Similarly, non-partitioning tracers are well established and will be well known to those of skill in the art.

Where one passive tracer and more than one partitioning tracer is used then equation 1 may be used two or more times, or a general equation developed.

REFERENCES

1. Cooke, C. E. J., *Method of Determining Fluid Saturation in Reservoirs*, 1971.
2. Jin, M., et al, *Partitioning tracer test for detection, estimation and remediation performance assessment of subsurface nonaqueous phase liquids*, Water resources research, 1995. 31(5): p. 1201-1211.
3. Deans, H. H., *Using chemical tracers to measure fractional flow and saturation in-situ*, in Fitlh Symposium on Improved Methods for Oil Recovery of the Society of Petroleum Engineers of AIME held In Tulsa, Okla., Apr. 16-19, 1978.1978, SPE: Tulsa, Okla.
4. Lichtenberger, G. J., *Field Applications of Interwell Tracers for Reservoir Characterization of Enhanced Oil Recovery Pilot Areas*, in SPE Production Operations Symposium1991, Society of Petroleum Engineers: Oklahoma City, Okla.
5. Zemel, B., *Tracers in Oil Field* 1994, New York: Elsevier.
6. Dias, F. F., Alexander, M, *Effect of Chemical Structure on the Biodegradability of Aliphatic Acids and Alcohols.* Applied Microbiology 22: p. 1114-1118.
7. Yang, H., et al., *Aromatic Compounds Biodegradation under Anaerobic Conditions and their QSBR Models.* Science of the Total Environment 358: p. 265-276.
8. Setarge, B., et al, *Partitioning and Interfacial Tracers to Characterize Non-Aqueous Phase Liquids (NAPLs) in Natural Aquifer Material*. Phys. Chem. Earth (B) 1999. 24: p. 501-510.

The invention will now be further illustrated by reference to the following non-limiting experimental examples:

EXPERIMENTS

Example 1

Thermal Stability

Oil and gas reservoirs generally have temperatures between 50° C. to 150° C. A tracer must therefore be stable at such temperatures for an extended period of time. Because of this, the tracer candidate was tested for thermal stability at different temperatures up to 150° C. for eight weeks.

The tests were conducted by adding a solution of the tracer candidates in formation water to a vial. The vial was sealed under an argon atmosphere and heated for eight weeks.

The results for 3,5-DFBOH are shown in FIG. 2 The x-axis represents temperatures in ° C. and the y-axis represents the recovery compared to a reference solution stored at −20° C. during the time course of the test.

As shown in FIG. 2 the tracer candidate demonstrates good thermal stability up to 150° C., allowing its use in petroleum reservoirs worldwide.

Example 2

Flow Properties and Passivity Towards the Reservoir Environment

Oil/water partitioning tracers have to follow the movement of the aqueous based fluids in an oil and gas reservoir with a predictable partitioning to the oil. It is therefore crucial that the tracer candidate follows the flow of injected water without interaction with the reservoir rock.

In addition the partitioning characteristics of the tracer candidate to the oil in the reservoir must be known. To test this, the tracer candidate was subjected to a test of flow and interaction properties in an oil environment as well as tests with certain rock materials. These tests are critical because many tracer candidates may have unwanted interactions and therefore are unsuited as tracers.

To test the possibility of interactions of the tracer candidate with reservoir rock, sorption tests with sandstone and limestone were performed. Sandstone and limestone are typical petroleum reservoir rock materials. 2 ml of a solution of the tracer candidates in formation water were added to vials containing 0.5 g sandstone or 0.5 g limestone. The vials were sealed under an argon atmosphere and heated for eight weeks up to 150° C.

The results are given in FIG. 3 and FIG. 4. The x-axis represents temperatures in ° C. and the y-axis represents the recovery compared to a reference solution stored at −20° C. during the time course of the test.

The results in FIG. 3 and FIG. 4 show that the tested tracer candidate has low interaction with the tested rock material and may therefore be suitable as a tracer in oil and gas reservoirs.

To test the dynamic properties of the tracer candidate an experimental setup containing a residual oil saturated column was used. The column had a length of 2 m and an internal diameter of 11.1 mm. The column was packed with 70 μm silica beads. Dead crude oil was pumped through the column after which artificial formation water was pumped through the system until residual oil saturation was reached. The tracer candidate was then co-injected with tritiated water (HTO) as a pulse into the water flow. The experiments were conducted with different oil types, different water compositions and at several temperatures.

The results from some of these experiments are given in FIG. 5, FIG. 6, FIG. 7 and FIG. 8. The tracer responses are plotted as a function of the accumulated water amount produced from the residual oil saturated column. The tracer responses are plotted as relative responses; all tracer concentrations for one compound are divided by the peak concentration for that compound.

The results from the dynamic flow experiments show that the partitioning tracer candidate is retained on the column compared to HTO meaning that it has a partition into the oil phase. Referring to FIG. 8, it can be seen that two different candidates show different degrees of partitioning to the oil. These tests indicate that the tested tracer candidates should act as partitioning tracers under reservoir conditions.

Example 3

Concentration and Detection Level

It is important that a tracer can be detected at as low concentrations in field samples and with as much certainty as possible. A partitioning tracer is injected into a field as a pulse (approximately 7-10% tracer (weight/weight)) into a water injection well. The amount of tracer required is a function of the total applicable reservoir volume to be traced and the limit of detection for the injected tracer. A low detection limit reduces the amount of tracer required for each field injection, giving an environmental and economic benefit.

Samples containing fluorinated benzyl alcohols are preconcentrated (solid phase extraction) and analysed with gas chromatography mass spectrometry (GC-MS). The different fluorinated benzyl alcohols are separated on a gas chromatography column. Specific detection is obtained using a mass spectrometer operating in single ion monitoring mode. This gives detection limits at 50 ppt concentrations. A chromatogram of a standard solution of selected fluorinated benzyl alcohols are given in FIG. 9.

It is appreciated that further development could allow even better detection limits. A typical concentration range detected in an oil producer in a partitioning tracer test performed by IFE (Institute for Energy Technology, Norway) is 50 ppt to 100 ppb.

Further analysis of blank samples from different oil fields around the world showed that the tracer candidates are not naturally present in the field and will thus not interfere with tracer studies (data not shown).

These tests verify the fluorinated benzyl alcohols applicability as partitioning tracers for the petroleum industry worldwide.

Example 4

Field Test

One field trial with the fluorinated benzyl alcohols have been performed in a relatively small field with short breakthrough times and one field test in a larger field is in progress.

In the completed field trial a selected fluorinated benzyl alcohol was injected together with the passive water tracer 2-FBA. Results from one of the production wells are given in FIG. 10. Due to re-injection of the produced water from the well, the plot of the produced tracer is not symmetrical. The pilot shows the applicability of tracers of this type and of the method. The test was successful and the tested tracer was verified and worked satisfactory giving accurate results for calculated oil saturation.

Example 5

Environmental Impact

The use of halogenated compounds is generally thought to have a negative effect on the environment and/or the ability to get regulatory approval for their use. On the Norwegian continental shelf (NCS) in particular, all compounds to be injected must be tested for their environmental impact according to stringent tests under Oslo-Paris Commission for the protection of the Marine Environment of the North-East and Atlantic. The results are summarized in the Harmonized Offshore Chemical Notification Format (HOCNF), which is used when applying for permit to use and discharge the chemicals to the sea on the NCS.

According to the HOCNF testing, a tested compound is environmentally classified with the label green, yellow, red or black according to the negative effect the compound is classified to have on the environment. It is very difficult to get permission for the use of black compounds, rendering their use unrealistic. Red compounds can be used, even though they are not preferred.

Tracers must be stable in the harsh reservoir environment, thus their results in the seawater biodegradation component of the HOCNF scheme "OECD (306 1999) guideline for testing chemicals, biodegradation in seawater" often show less than 20% biodegradation ensuring that they automatically are placed in the red category.

In addition to biodegradation in seawater other tests to be conducted are the toxicity test with Acardia Tonsa (ISO14669; 1999), providing a median lethal concentration (LC50) after an exposure of 48 hr, toxicity test with Skeletonema Costatum (ISO 10253; 2006), providing a median effect concentration (EC50/EL50) after an exposure of 72 hr, toxicity test with Scophthalmus Maximus (PARCOM 2006), providing the mortality of fish after 96 hr at EC50 value and bioaccumulation potential (OECD Guidelines for Testing of Chemicals, 117), providing the logarithm of n-octanol/water partition coefficient.

The most important environmental properties were tested on several example compounds. These are biodegradability in seawater and toxicity screening for Skeletonema Costatum. The latter gives a good general indication of the total toxicity of a chemical and in combination with the biodegradability gives a strong indication of the total impact of the environment. The results are given in Table 2.

TABLE 2

Results from screening of environmental properties for five selected fluorinated benzyl alcohols.

| | Toxicity $EL_{50}$ mg/L | Biodegradability $BOD_{28}$ % |
|---|---|---|
| 4-FBOH | Ca 10 | 3 |
| 2,6-DFBOH | >10 <100 | 0 |
| 2,3,6-TFBOH | >100 <1000 | 2 |
| 2,4,6-TFBOH | >10 <100 | 0-3 |
| 3,5-DFBOH | >100 <1000 | 2 |

The results given in Table 2 indicate that the tested fluorinated benzyl alcohols will be classified as red chemicals. This is the same category as most of the existing water tracers and thus should receive regulatory approval.

Accordingly, the tracer candidates of the invention may be used as partitioning tracers in oil and gas reservoirs.

What is claimed is:

1. A method for assessing the oil saturation of an oil field having an injection well and a production well, said method comprising:
   a) injecting at least a first tracer having a first partition coefficient and a second tracer having a second partition coefficient into said injection well;
   b) measuring the presence and/or concentration over time of said first tracer and said second tracer in produced water from said production well;
   c) determining the retention times for each of said first tracer and said second tracer
   d) relating the retention times and partition coefficients of each of said first and second tracers to oil saturation of said oil field whereon said first tracer, and optionally said second tracer is a benzyl alcohol of formula i)

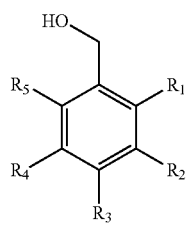

wherein each of $R_1$ to $R_5$ is independently selected from H, F, Cl, Br, I, $CF_3$, $CF_2Cl$, $CFCl_2$ and $CCl_3$ and wherein at least one of $R_1$ to $R_5$ is not H; and
wherein said at least one benzyl alcohol of formula i) is at least one chlorinated benzyl alcohol of any or formulae Cl1 to Cl26;

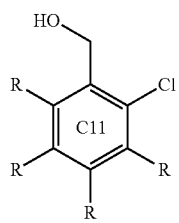 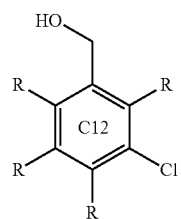

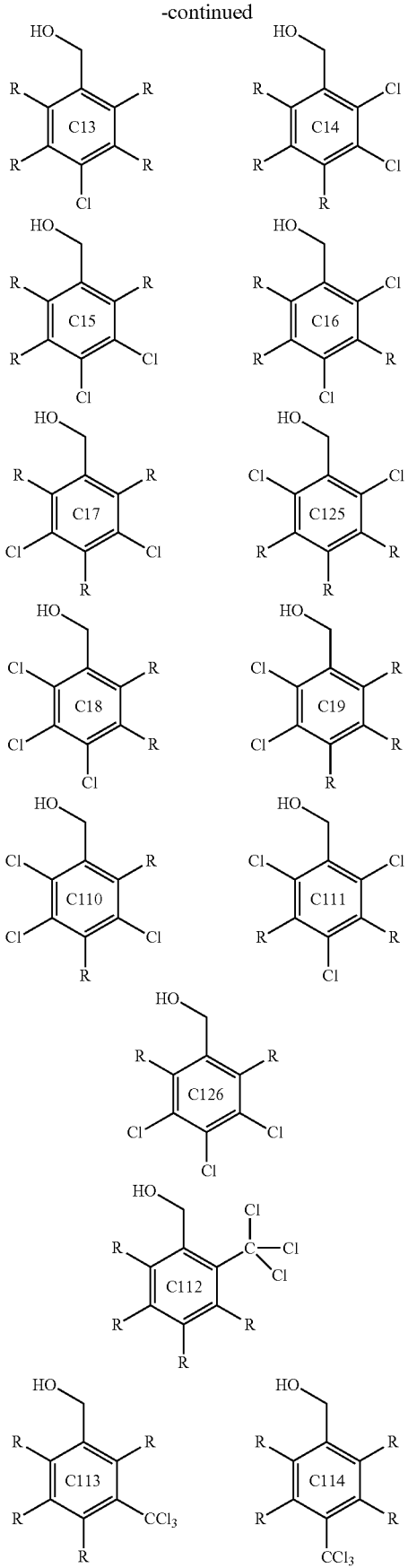

-continued

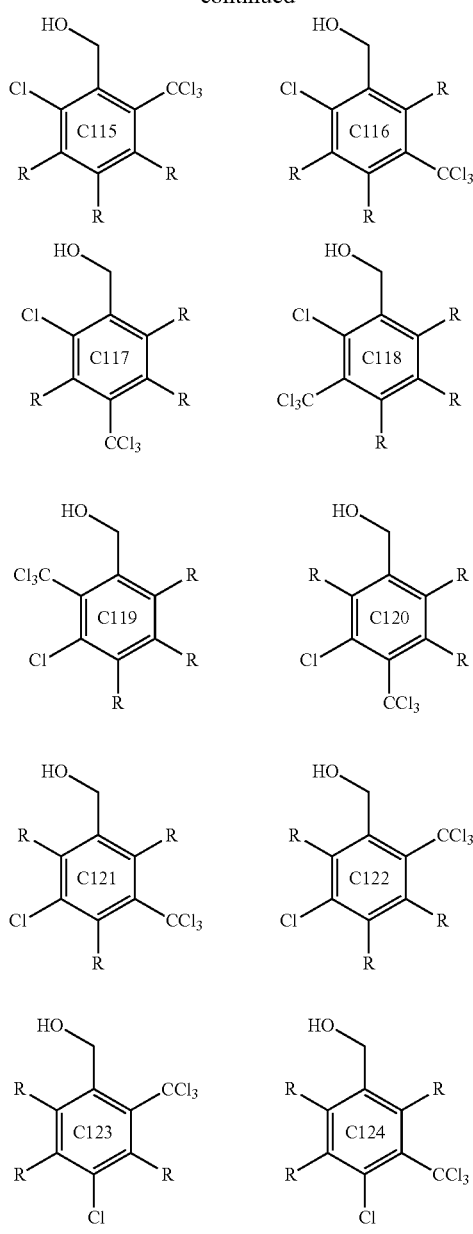

wherein all R groups in formulae C11 to C126 are hydrogen.

2. A method for assessing the oil saturation of an oil field having an injection well and a production well, said method comprising:
   a) injecting at least a first tracer having a first partition coefficient and a second tracer having a second partition coefficient into said injection well;
   b) measuring the presence and/or concentration over time of said first tracer and said second tracer in produced water from said production well;
   c) determining the retention times for each of said first tracer and said second tracer
   d) relating the retention times and partition coefficients of each of said first and second tracers to oil saturation of said oil field whereon said first tracer, and optionally said second tracer is a benzyl alcohol of formula i)

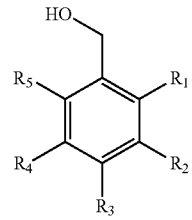

wherein each of $R_1$ to $R_5$ is independently selected from H, F, Cl, Br, I, $CF_3$, $CF_2Cl$, $CFCl_2$ and $CCl_3$ and wherein at least one of $R_1$ to $R_5$ is not H;
    wherein said at least one benzyl alcohol of formula i) is at least one fluorinated benzyl alcohol of any or formulae F1 to F26:

F1

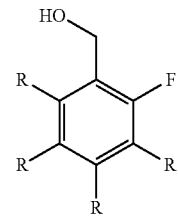

F2

F3

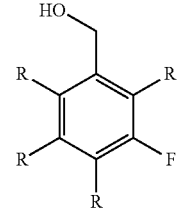

F4

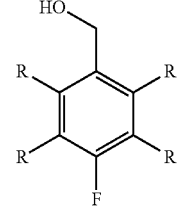

F5

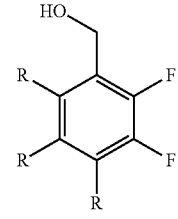

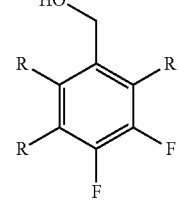

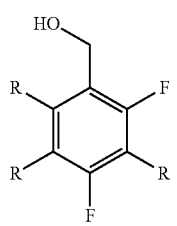 F6
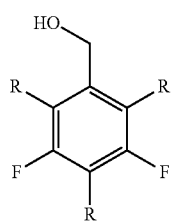 F7
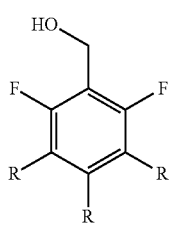 F25
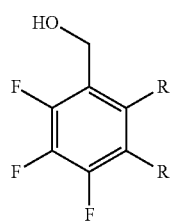 F8
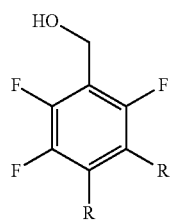 F9
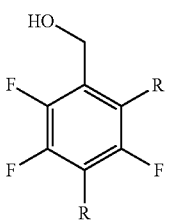 F10
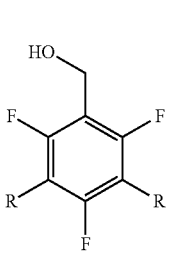 F11
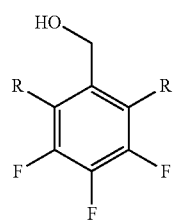 F26
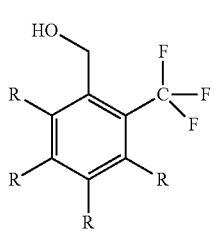 F12
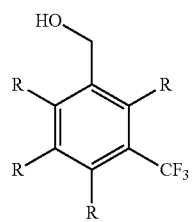 F13
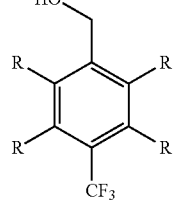 F14
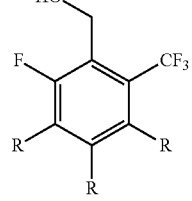 F15
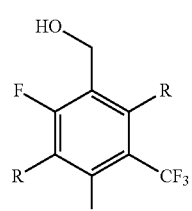 F16
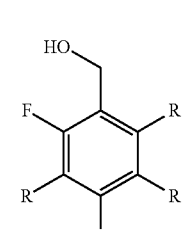 F17

-continued

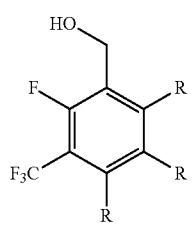
F18

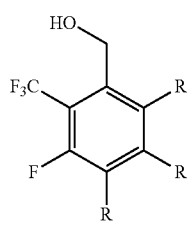
F19

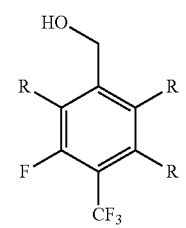
F20

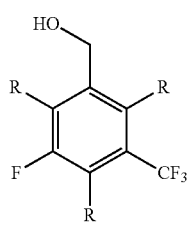
F21

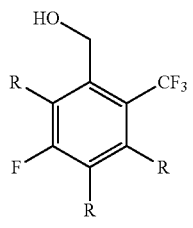
F22

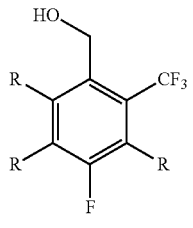
F23

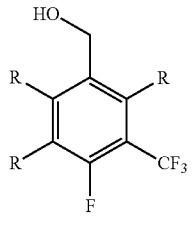
F24 wherein each R group is independently selected from H, Cl, Br, I, $CF_2Cl$, $CFCl_2$ and $CCl_3$, Preferably each R group is independently selected from H and Cl.

3. A method for assessing the oil saturation of an oil field having an injection well and a production well, said method comprising:

a) injecting at least a first tracer having a first partition coefficient and a second tracer having a second partition coefficient into said injection well;

b) measuring the presence and/or concentration over time of said first tracer and said second tracer in produced water from said production well;

c) determining the retention times for each of said first tracer and said second tracer d) relating the retention times and partition coefficients of each of said first and second tracers to oil saturation of said oil field whereon said first tracer, and optionally said second tracer is a benzyl alcohol of formula i)

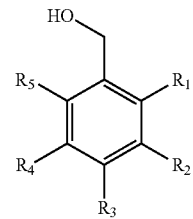

i)

wherein each of $R_1$ to $R_5$ is independently selected from H, F, Cl, Br, I, $CF_3$ $CF_2Cl$, $CFCl_2$ and $CCl_3$ and wherein at least one of $R_1$ to $R_5$ is not H;

wherein said at least one benzyl alcohol of formula i) is at least one fluorinated benzyl alcohol of any or formulae F1 to F26:

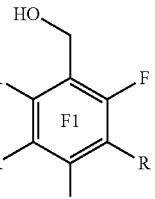 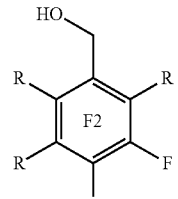

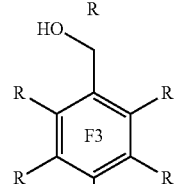 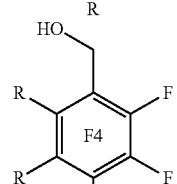

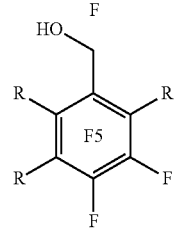 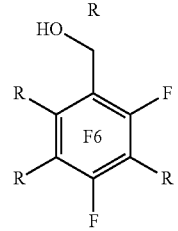

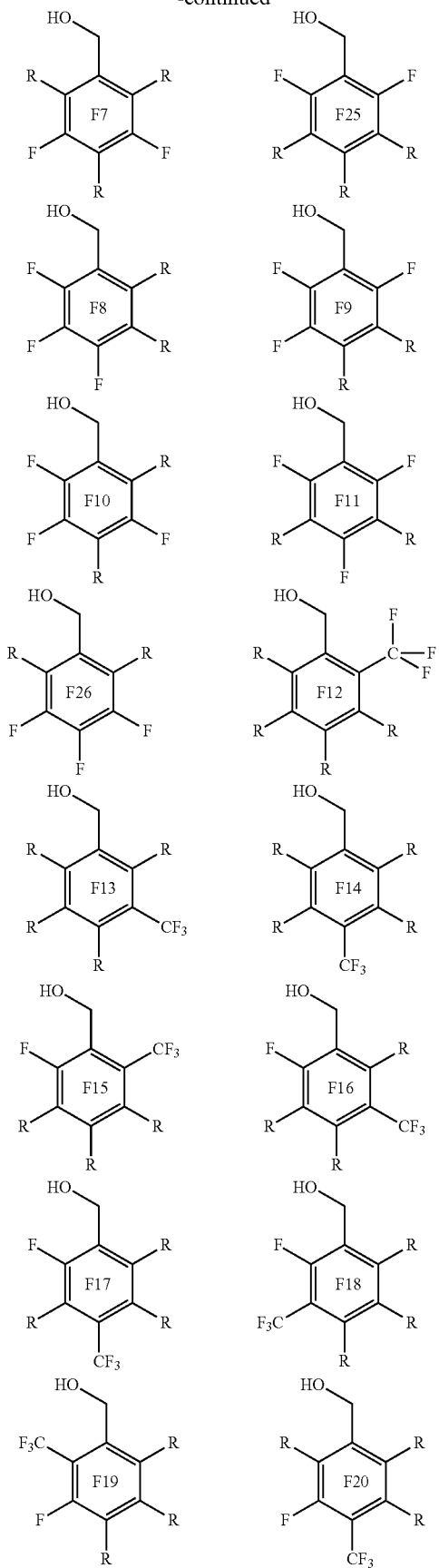

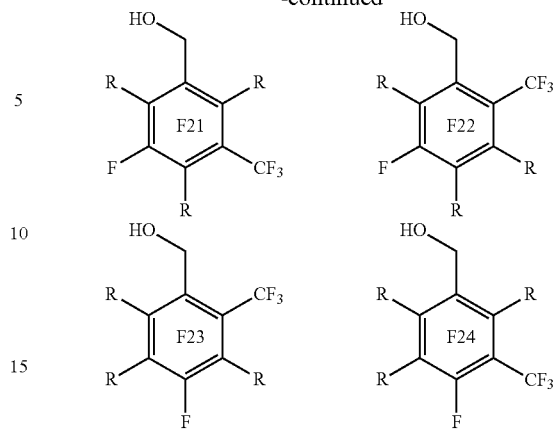

wherein all R groups in formulae F1 to F26 are hydrogen.
4. The method of claim 2, wherein 1, 2 or 3 R groups of formulae F1 to F26 are Cl.
5. A method for assessing the oil saturation of an oil field having an injection well and a production well, said method comprising:
 a) injecting at least a first tracer having a first partition coefficient and a second tracer having a second partition coefficient into said injection well;
 b) measuring the presence and/or concentration over time of said first tracer and said second tracer in produced water from said production well;
 c) determining the retention times for each of said first tracer and said second tracer
 d) relating the retention times and partition coefficients of each of said first and second tracers to oil saturation of said oil field whereon said first tracer, and optionally said second tracer is a benzyl alcohol of formula i)

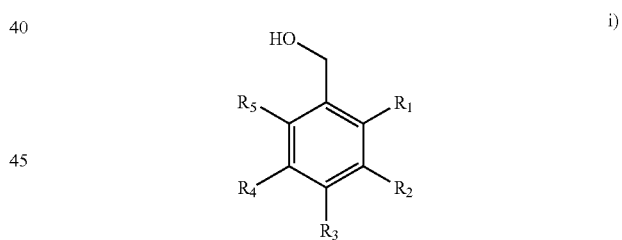

wherein each of $R_1$ to $R_5$ is independently selected from H, F, Cl, Br, I, $CF_3$ $CF_2Cl$, $CFCl_2$ and $CCl_3$ and wherein at least one of $R_1$ to $R_5$ is not H; and;
wherein said at least on benzyl alcohol of formula i) is at least one chlorinated benzyl alcohol of any or formulae Cl1 to Cl26:

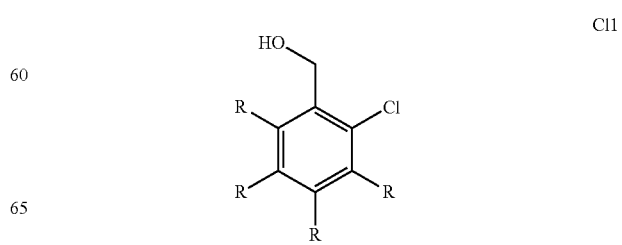

| | | | |
|---|---|---|---|
| 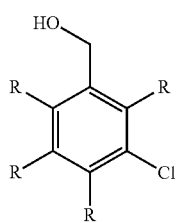 | Cl2 | 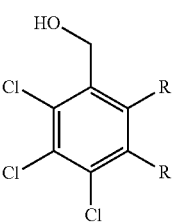 | Cl8 |
| 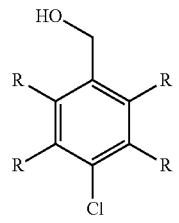 | Cl3 | 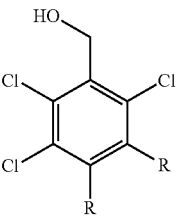 | Cl9 |
| 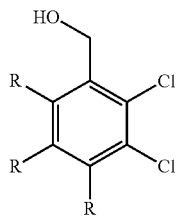 | Cl4 | 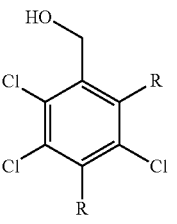 | Cl10 |
| 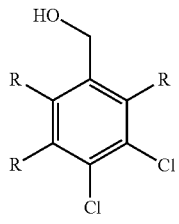 | Cl5 | 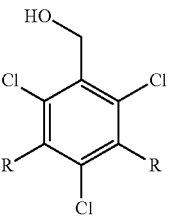 | Cl11 |
| 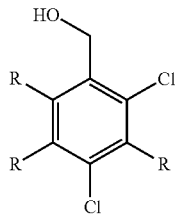 | Cl6 | 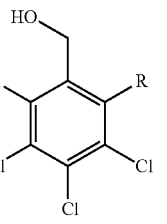 | Cl126 |
| 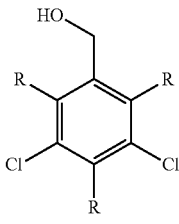 | Cl7 | 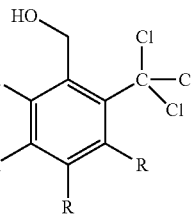 | Cl12 |
| 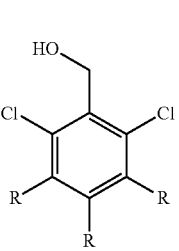 | Cl25 | 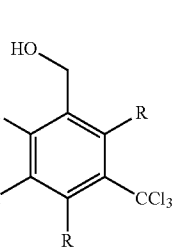 | Cl13 |

Cl14 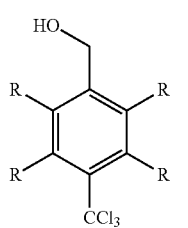
Cl15 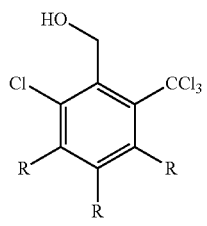
Cl16 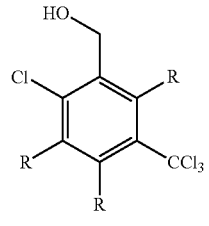
Cl17 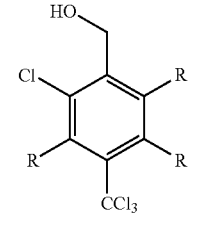
Cl18 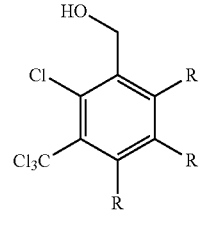
Cl19 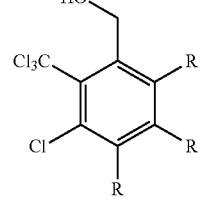
Cl20 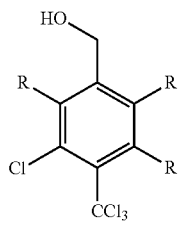
Cl21 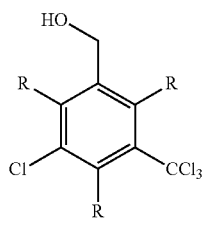
Cl22 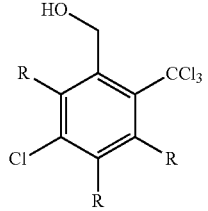
Cl23 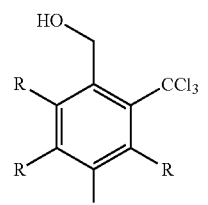
Cl24 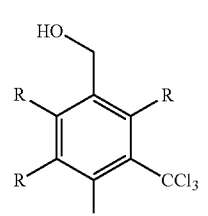
wherein 1, 2 or 3 R groups of formulae Cl1 to Cl26 are F.
* * * * *